United States Patent
Aki et al.

(10) Patent No.: US 9,586,892 B2
(45) Date of Patent: Mar. 7, 2017

(54) PENTENENITRILE ISOMERIZATION

(71) Applicant: INVISTA NORTH AMERICA S.A R.L., Wilmington, DE (US)

(72) Inventors: Sudhir N. V. K. Aki, Katy, TX (US); William J. Tenn, III, Beaumont, TX (US); Thomas E. Vos, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/649,634

(22) PCT Filed: Dec. 5, 2013

(86) PCT No.: PCT/US2013/073392
§ 371 (c)(1),
(2) Date: Jun. 4, 2015

(87) PCT Pub. No.: WO2014/089343
PCT Pub. Date: Jun. 12, 2014

(65) Prior Publication Data
US 2015/0368189 A1 Dec. 24, 2015

Related U.S. Application Data

(60) Provisional application No. 61/734,535, filed on Dec. 7, 2012.

(30) Foreign Application Priority Data

Mar. 15, 2013 (GB) .................................. 1304799.8

(51) Int. Cl.
*C07C 253/30* (2006.01)
(52) U.S. Cl.
CPC .................... *C07C 253/30* (2013.01)

(58) Field of Classification Search
CPC .............................. C07C 253/30; C07C 255/07
See application file for complete search history.

(56) References Cited

U.S. PATENT DOCUMENTS 3,526,654 A 9/1970 Hildebrand
2006/0194979 A1* 8/2006 Bartsch ................ C07C 253/30
558/462

FOREIGN PATENT DOCUMENTS

WO 2004/094364 A 11/2004

OTHER PUBLICATIONS

"Puralox/Catalox® High Purity Activated Aluminas" SASOL, Online available at <http://www.sasoltechdata.com/tds/PURALOX_CATALOX.pdf>, 2005, 9 pages.
Misra, Chanakaya, "Industrial Alumina Chemicals", American Chemical Society, vol. 59, Issue 10, 1986, pp. 706A-706A.
International Search Report Received for PCT Application No. PCT/US2013/073392, mailed on Feb. 19, 2014, 3 pages.
International Preliminary Report on Patentability and Written Opinion Received for PCT Application No. PCT/US2013/073392, issued on Jun. 9, 2015, 5 pages.

* cited by examiner

*Primary Examiner* — Valerie Rodriguez-Garcia
(74) *Attorney, Agent, or Firm* — Robert B. Furr, Jr.; Edward F. Kenehan, Jr.

(57) ABSTRACT

Pentenenitrile oligomers formed in a process for isomerizing cis-2-pentenenitrile to 3-pentenenitrile are minimized in the presence of an aluminum oxide catalyst. The process comprises providing an aluminum oxide catalyst having an alkali metal and/or alkaline earth metal and/or iron content, measured in the form of alkali metal oxide and/or alkaline earth metal oxide and/or iron oxide, respectively of less than 5000 ppm by weight.

15 Claims, 1 Drawing Sheet

PENTENENITRILE ISOMERIZATION

CROSS-REFERENCE TO RELATED APPLICATIONS

This application claims benefit of the filing date of U.S. Provisional Patent Application No. 61/734,535, filed Dec. 7, 2012 and Great Britain Patent Application No. 1304799.8 filed on Mar. 15, 2013, the contents of which are all specifically incorporated herein by reference in their entireties.

The present invention relates to a process for isomerizing cis-2-pentenenitrile to 3-pentenenitrile and, in particular, to the use of aluminium oxides to catalyze such a reaction.

BACKGROUND OF THE INVENTION

Commercial processes for producing adiponitrile, an important intermediate in the manufacture of nylon-6,6 and related products, typically include a stage in which 3-pentenenitrile (or 4-pentenenitrile) is hydrocyanated in the presence of nickel (0) catalyst to form adiponitrile. It is known that cis-2-pentenenitrile is formed as a byproduct during such a hydrocyanation. The formation of cis-2-pentenenitrile represents an adiponitrile yield loss in the process. Furthermore, the accumulation of cis-2-pentenenitrile during the hydrocyanation reaction is undesirable because it behaves as a catalyst poison. However, the removal of cis-2-pentenenitrile is not straightforward. It can be separated from unreacted 3-pentenenitrile by distillation. Alternatively, it can be removed by reaction with an alkali metal sulfite and bisulfite solution but this can complicate the procedure. With this in mind, rather than physically removing the cis-2-pentenenitrile, efforts have focused on converting it to a useful product. In this regard, it is preferred to isomerize cis-2-pentenenitrile to 3-pentenenitrile, which can then be recycled back into the hydrocyanation reaction.

The isomerization of cis-2-pentenenitrile to 3-pentenenitrile has been described in U.S. Pat. No. 3,526,654 and U.S. Patent Publication No. 2006/0194979. Both describe that the isomerization reaction may be carried out in the presence of an aluminium oxide catalyst. In U.S. Pat. No. 3,526,654, the aluminium oxide catalyst used is Alcoa F-1, while in U.S. Patent Publication No. 2006/0194979, the aluminium oxide catalyst has a BET surface area of at least 50 m$^2$/g.

SUMMARY OF THE INVENTION

Against this background, the present inventors have found that while, from an economical point of view, it is desirable to use aluminium oxide catalysts for catalysing the isomerization of cis-2-pentenenitrile to 3-pentenenitrile, there are associated drawbacks. In particular, the inventors have found that the aluminium oxides conventionally used have a limited lifetime and lead to the production of unacceptably high levels of byproducts.

More specifically, the inventors have identified that during the aluminium oxide-catalyzed isomerization of cis-2-pentenenitrile to 3-pentenenitrile, there are two competing reactions taking place; firstly the target isomerization reaction and secondly, an oligomerization reaction. It seems that the accumulation of byproducts and the limited lifetime of the aluminium catalysts can be attributed to this oligomerization reaction. In particular, the initial products of the oligomerization reaction are C10-dinitriles (DDNs), which can be problematic even at low levels. In this regard, pentenenitrile oligomers behave as catalyst poisons as they accumulate and the samples become more viscous as the oligomerization reaction progresses, and the catalyst becomes coated in heavies. Furthermore, if the target adiponitrile product contains DDNs (which it will if the 3-pentenenitrile produced contains DDNs), some of the DDNs will form cyclic Schiff bases when the adiponitrile is subsequently hydrogenated to hexamethylenediamine. These cyclic Schiff bases behave as chain terminators during the subsequent synthesis of nylon-6,6, producing a lower quality nylon polymer.

Following an extensive investigation of the reactions which are taking place, the inventors have identified that there is a link between the presence of alkali metals and/or alkaline earth metals and/or iron in the aluminium oxide catalyst and the degree to which pentenenitrile oligomers, such as DDNs, accumulate during the isomerization reaction. In this regard, the inventors have found that the higher the alkali metal and/or alkaline earth metal and/or iron content of the aluminium oxide catalyst, the higher the levels of pentenenitrile oligomers produced and the shorter the lifetime of the catalyst. On the basis of this work, it has become clear that it is advantageous when isomerizing cis-2-pentenenitrile to 3-pentenenitrile to carry out the reaction in the presence of an aluminium oxide catalyst having a minimal alkali metal and/or alkaline earth metal and/or iron content.

Therefore, the present invention provides a process for isomerizing cis-2-pentenenitrile to 3-pentenenitrile in the presence of an aluminium oxide catalyst, wherein the aluminium oxide catalyst has an alkali metal and/or alkaline earth metal and/or iron content, measured in the form of alkali metal oxide and/or alkaline earth metal oxide and/or iron oxide, respectively, of less than 5000 ppm by weight.

Advantageously, where an aluminium oxide catalyst having a low content of alkali metal and/or alkaline earth metal and/or iron is used, the formation of unwanted byproducts, specifically pentenenitrile oligomers, is minimised and the lifetime of the catalyst is improved. A further advantage which has been identified is that the selectivity of the isomerization reaction for 3-pentenenitrile increases as the alkali metal or alkaline earth metal or iron content of the aluminium oxide catalyst decreases.

Therefore, the present invention provides a method for minimising the amount of pentenenitrile oligomers formed in a process for isomerizing cis-2-pentenenitrile to 3-pentenenitrile in the presence of an aluminium oxide catalyst; said method comprising providing an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight.

Also provided by the present invention is the use of an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight for minimising the amount of pentenenitrile oligomers formed in a process for isomerizing cis-2-pentenenitrile to 3-pentenenitrile.

The present invention further provides a method for increasing the degree of selectivity for 3-pentenitrile in a process for isomerizing cis-2-pentenenitrile to 3-pentenenitrile in the presence of an aluminium oxide catalyst; said method comprising providing an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight.

Also provided by the present invention is the use of an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight for increasing the degree of selectivity for 3-pentenitrile in a process for isomerizing cis-2-pentenenitrile to 3-pentenenitrile.

The present invention further provides a method for improving the lifetime of an aluminium oxide catalyst in a process for isomerizing cis-2-pentenenitrile to 3-pentenenitrile; said method comprising providing an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight.

Also provided by the present invention is the use of an aluminium oxide catalyst having an alkali metal and/or alkaline earth metal and/or iron content, measured in the form of alkali metal oxide and/or alkaline earth metal oxide and/or iron oxide, respectively of less than 5000 ppm by weight for improving the lifetime of an aluminium oxide catalyst in a process for isomerizing cis-2-pentenenitrile to 3-pentenenitrile.

The isomerization process of the present invention is carried out by contacting the cis-2-pentenenitrile with the solid state aluminium oxide catalyst in either the liquid phase or the vapour phase. In one embodiment, the process is carried out in the liquid phase. The process is carried out at a temperature in the range from 50 to 250° C., in one embodiment, at a temperature in the range from 125 to 200° C. The pressure at which the isomerization reaction is performed is not critical and pressures in the range from 0.5 to 50 atmospheres are acceptable.

The isomerization process may be carried out in any reactor which is capable of containing a liquid or gaseous medium. An example of suitable apparatus is an evaporator for feeding cis-2-pentenenitrile in the vapour phase to a column containing the catalyst. Preferably, the isomerization process is carried out in a reactor capable of containing a liquid feed and the catalyst is in the form of a packed bed.

The source of the cis-2-pentenenitrile used as the starting material in the process of the invention is not limited although it will typically have been obtained as a by-product during the hydrocyanation of 3-pentenenitrile and 4-pentenenitrile in the presence of a Ni(0) catalyst in the production of adiponitrile.

The isomerization reaction of the present invention takes place in the presence of an aluminium oxide catalyst which has a low content of alkali metals and/or alkaline earth metals and/or iron. Conventionally, the choice of aluminium oxide used to catalyze this isomerization reaction has been driven by economic factors. An example of a commercially available aluminium oxide which has been used is Alcoa F-1 (available from Alcoa) which is stated to have a sodium content (in the form of $Na_2O$) of about 5800 ppm. However, as described above, the inventors have found that these aluminium oxide catalysts have comparatively short lifetimes and lead to the generation of unacceptably high levels of pentenenitrile oligomer byproducts when used to catalyze the isomerization of cis-2-pentenenitrile to 3-pentenenitrile.

Standard analytical techniques for determining metal content typically measure the content of alkali metal and/or alkaline earth metal and/or iron metal impurities as the corresponding alkali metal, alkaline earth metal or iron oxides. Hence, the alkali metal and/or alkaline earth metal and/or iron contents of the aluminium oxide catalysts used in the methods of the present invention are as measured in the form of the corresponding alkali metal oxide, alkaline earth metal oxide and/or iron oxide, respectively. For example, where the alkali metal is sodium, the sodium content is measured as $Na_2O$. Examples of techniques which may be used to determine the alkali metal and/or alkaline earth metal and/or iron contents of the catalysts used in the methods of the invention include atomic absorption and flame photometry methods, such as described in Industrial Alumina Chemicals, ACS Monograph 184, Chanakaya Misra, American Chemical Society, 1986.

In one embodiment, the aluminium oxide catalyst used in the process of the present invention has an alkali metal content, measured in the form of alkali metal oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight.

In one embodiment, the alkali metal is selected from sodium and potassium, in one embodiment, sodium. In this regard, preferably, the aluminium oxide catalyst used in the process of the present invention has a sodium content of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight.

Alternatively or in addition, the aluminium oxide catalyst used in the process of the present invention has an alkaline earth metal content, measured in the form of alkaline earth metal oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight.

In one embodiment, the alkaline earth metal is selected from calcium or magnesium.

Alternatively or in addition, the aluminium oxide catalyst used in the process of the present invention has an iron content, measured in the form of iron oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight.

Advantageously, the aluminium oxide catalyst used in the process of the present invention has a combined content of alkali and alkaline earth metal, measured in the form of alkali metal oxide and alkaline earth metal oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight.

In one embodiment, the aluminium oxide catalyst used in the process of the present invention has a combined content of alkali and alkaline earth metal, measured in the form of alkali metal oxide and alkaline earth metal oxide of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight, wherein the alkali metal is selected from sodium or potassium and the alkaline earth metal is selected from calcium or magnesium.

In one embodiment, the aluminium oxide catalyst used in the process of the present invention has a combined content of alkali metal and iron, measured in the form of alkali metal oxide and iron oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight, in one embodiment, wherein the alkali metal is selected from sodium or potassium.

In one embodiment, the aluminium oxide catalyst used in the process of the present invention has a combined content of alkaline earth metal and iron, measured in the form of alkaline earth metal oxide and iron oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight, in one embodiment, wherein the alkali metal is selected from calcium or magnesium.

Advantageously, the aluminium oxide catalyst used in the process of the present invention has a combined content of alkali metal, alkaline earth metal and iron, measured in the form of alkali metal oxide, alkaline earth metal oxide and iron oxide, of less than 5000 ppm by weight, in one embodiment less than 3000 ppm by weight, preferably less than 1000 ppm by weight, preferably less than 500 ppm by weight, preferably less than 100 ppm by weight, preferably less than 50 ppm by weight, preferably less than 10 ppm by weight, preferably less than 8 ppm by weight, in one embodiment, wherein the alkali metal is selected from sodium or potassium and the alkaline earth metal is selected from calcium or magnesium.

Aluminium catalysts which may be used in the process of the present invention are commercially available. Examples of suitable aluminium oxide catalysts for use in the process of the present invention include AL-4126, AL-3996 and AL-3995, which are all commercially available from Engelhard and Catalox SCFa-140 and Catalox SBa-200, which are commercially available from Sasol. Suitable aluminium oxide catalysts may be prepared using the techniques described in the Sasol "Puralox/Catalox® High Purity activated aluminas" Sasol product brochure (http://www.sasoltechdata.com/tds/PURALOX_CATALOX.pdf), wherein aluminium alkoxide is used to produce synthetic boehmite of high purity.

As described above, by using the described aluminium oxide catalysts in the isomerization method of the present invention, several advantages are observed, specifically, a reduction in the production of unwanted pentenenitrile byproducts, an improvement in selectivity for 3-pentenenitrile and an improved catalyst lifetime.

In an industrial adiponitrile plant, it is important that the adiponitrile produced has a low content of unwanted pentenenitrile oligomers such as DDN. From a commercial perspective, this limit is typically of the order of about 500 ppm by weight or less. There are several steps in which unwanted pentenenitrile oligomers, in particular DDNs, may be generated during the production of adiponitrile and the isomerization step with which the present invention is concerned is just one of these steps. Therefore, it is important that the levels of DDNs produced in the process of the present invention are as low as possible. In this regard, preferably the maximum level of DDN formation during the isomerization process of the present invention is less than about 300 ppm by weight, in one embodiment less than about 200 ppm for every 10 wt % of cis-2-pentenenitrile starting material which is converted to 3-pentenenitrile and trans-2-pentenenitrile products.

In particular, the inventors have determined that the ratio of C10-dinitriles (DDNs) formed (wt %)/total of 3-pentenenitriles and trans-2-pentenenitriles (PNs) formed (wt %) that is acceptable is about 350 or less, preferably about 300 or less, preferably about 250 or less, preferably about 200 or less, preferably about 150 or less, preferably about 100 or less. The amount of DDNs formed and the amount of PNs formed are measurements with which the skilled person will be familiar.

By virtue of the particular aluminium oxide catalysts used, the process of the present invention provides a high degree of selectivity for 3-pentenenitrile. In one embodiment, the isomerization process of the present invention has a degree of selectivity for 3-pentenenitrile of about 60% or more, in one embodiment, about 70% or more, in one embodiment, about 80% or more, in one embodiment, about 90% or more.

DESCRIPTION OF THE FIGURES

The invention will now be described further by reference to the following figures and examples which are not intended to be limiting on the scope of the claim.

EXAMPLES

Example 1

The experiment was conducted in a 10 mL serum bottle, using a temperature-regulated aluminum heating block. Mixing was accomplished using a magnetic stir bar. The heating block was enclosed in a nitrogen purge box. Serum bottles were charged with F-200 (commercially available from Alcoa) aluminum oxide 0.5 g, and cis-2-pentenenitrile (4.5 grams) inside a glove-box and then transferred to the heating block at the beginning of the experiment. The temperature of the heating block was maintained at 100° C. Samples were then removed at the desired intervals for analysis by gas chromatography.

Example 2

Example 1 was repeated except that AL-4126 aluminum oxide (commercially available from Engelhard) was used as the catalyst.

Example 3

Example 1 was repeated except that AL-3996 aluminum oxide (commercially available from Engelhard) was used as the catalyst.

Example 4

Example 1 was repeated except that AL-3995 aluminum oxide (commercially available from Engelhard) was used as the catalyst.

Example 5

Example 1 was repeated except that Catalox SCFa-140 aluminum oxide (commercially available from Sasol) was used as the catalyst.

Example 6

Example 1 was repeated except that sodium-modified aluminum oxide ($Na/Al_2O_3$) was used as the catalyst.

Preparation of Sodium Modified Alumina:

A ceramic mortar and pestle was used to prepare a sodium-modified aluminum oxide catalyst material that contained 1 percent by weight (wt %) sodium based on the combined weight percent of the precursor aluminum oxide and sodium hydroxide. The material was then dried under vacuum at minus 25 inches of mercury at 300° C. for 18 hours, and then allowed to cool under nitrogen prior to evaluation.

The results of the evaluation of Examples 1 to 6, which have varying sodium contents, are shown in Table 1 below.

TABLE 1

| Example | Catalyst | $Na_2O$ (ppm)[†] | DDN (wt %)/PNs formed (wt %) |
|---|---|---|---|
| 1 | F-200 | 3000 | 254 |
| 2 | AL-4126 | 800 | 97 |
| 3 | AL-3996 | 600 | 131 |
| 4 | AL-3995 | 600 | 112 |
| 5 | Catalox SCFa-140 | 5.5 | 36 |
| 6 | $Na/Al_2O_3$ | 10000[‡] | 727 |

[†]levels of $Na_2O$ as reported from the manufacturer.
[‡]Aldrich alumina + 1 wt % NaOH, and calcined at 300° C./16 hours prior to evaluation.
PN formed = trans-3-pentenenitrile, cis-3-pentenenitrile, and trans-2-pentenenitrile formed.

Figure 1:
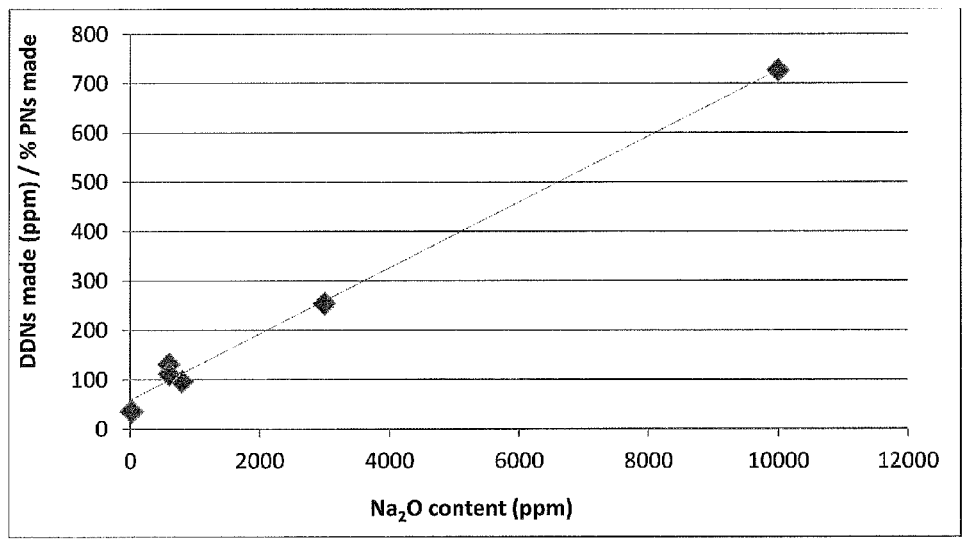
FIG. 1 illustrates the correlation between the formation of byproducts due to cis-2-pentenenitrile dimerization and the sodium content of the aluminum oxide catalysts of examples 1 to 6.
Figure 2:
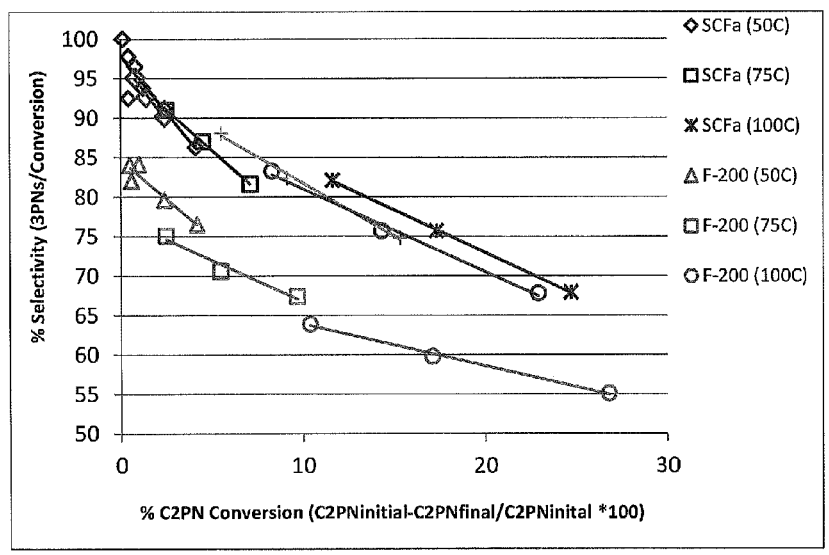
FIG. 2 illustrates the correlation between cis-2-pentenenitrile conversion and selectivity to 3-pentenenitriles using the aluminium oxide catalysts of Examples 7 to 15 which have varying sodium contents.

The data presented in Table 1 show the effect of varying the sodium content of aluminum oxide catalysts used for isomerization of cis-2-pentenenitrile to 3-pentenenitriles. The data show that the formation of by-products formed by dimerization of 2-PN (i.e. C10-dinitriles) increases linearly as sodium content increases. This can also be seen in FIG. 1.

Example 7

The experiment was conducted in a 10 mL serum bottle, using a temperature-regulated aluminum heating block. Mixing was accomplished using a magnetic stir bar. The heating block was enclosed in a nitrogen purge box. Serum bottles were charged with F-200 (commercially available from Alcoa) aluminum oxide 0.5 g, and cis-2-pentenenitrile (4.5 grams) inside a glove-box and then transferred to the heating block at the beginning of the experiment. The temperature of the heating block was maintained at 50° C. Samples were then removed at the desired intervals for analysis by gas chromatography.

Example 8

Example 7 was repeated except that the temperature of the heating block during the experiment was maintained at 75° C.

Example 9

Example 7 was repeated except that the temperature of the heating block during the experiment was maintained at 100° C.

Example 10

Example 7 was repeated except that Catalox SCFa-140 alumina (commercially available from Sasol) was used as the catalyst, and the temperature of the heating block during the experiment was maintained at 50° C.

Example 11

Example 10 was repeated except that the temperature of the heating block during the experiment was maintained at 75° C.

Example 12

Example 10 was repeated except that the temperature of the heating block during the experiment was maintained at 100° C.

Example 13

Example 7 was repeated except that AL-3996 alumina (commercially available from Engelhard) was used as the catalyst, and the temperature of the heating block during the experiment was maintained at 50° C.

Example 14

Example 13 was repeated except that the temperature of the heating block during the experiment was maintained at 100° C.

Example 15

Example 7 was repeated except that Catalox SBa-200 alumina (commercially available from Sasol) was used as the catalyst, and the temperature of the heating block during the experiment was maintained at 50° C.

The results of Examples 7 to 15 are shown in Table 2 below.

TABLE 2

| Example | Catalyst | $Na_2O$ (ppm)[†] | Temperature (° C.) | % C2PN conversion (X) | % Selectivity (3PNs/X) |
|---|---|---|---|---|---|
| 7 | F-200 | 3000 | 50 | 1.0 | 84.1 |
|   |       |      |    | 2.4 | 79.6 |
|   |       |      |    | 4.2 | 76.5 |
|   |       |      |    | 0.5 | 84.0 |
|   |       |      |    | 0.6 | 82.0 |
| 8 | F-200 | 3000 | 75 | 2.5 | 75.1 |
|   |       |      |    | 5.5 | 70.6 |

TABLE 2-continued

| Example | Catalyst | Na$_2$O (ppm)[†] | Temperature (° C.) | % C2PN conversion (X) | % Selectivity (3PNs/X) |
|---|---|---|---|---|---|
|  |  |  |  | 9.7 | 67.4 |
| 9 | F-200 | 3000 | 100 | 10.4 | 63.9 |
|  |  |  |  | 17.1 | 59.8 |
|  |  |  |  | 26.8 | 55.1 |
| 10 | SCFa | 5.5 | 50 | 0.1 | 100 |
|  |  |  |  | 0.4 | 97.8 |
|  |  |  |  | 0.8 | 96.5 |
|  |  |  |  | 1.2 | 93.8 |
|  |  |  |  | 2.4 | 91.2 |
|  |  |  |  | 4.1 | 86.3 |
| 11 | SCFa | 5.5 | 75 | 2.5 | 91.0 |
|  |  |  |  | 4.5 | 87.0 |
|  |  |  |  | 7.1 | 81.6 |
| 12 | SCFa | 5.5 | 100 | 11.6 | 82.1 |
|  |  |  |  | 17.3 | 75.7 |
|  |  |  |  | 24.7 | 67.9 |
| 13 | AL-3996 | 600 | 50 | 0.8 | 95.1 |
|  |  |  |  | 1.4 | 92.7 |
|  |  |  |  | 2.4 | 90.2 |
| 14 | AL-3996 | 600 | 100 | 8.3 | 83.3 |
|  |  |  |  | 14.3 | 75.7 |
|  |  |  |  | 22.9 | 67.8 |
| 15 | SBa | 150 | 100 | 5.1 | 88.1 |
|  |  |  |  | 9.1 | 82.4 |
|  |  |  |  | 15.3 | 74.8 |

[†]Levels of Na$_2$O as reported from the manufacturer.

The data presented in Table 2 show the effect of varying sodium content of aluminum oxide catalysts used for isomerization of cis-2-pentenenitrile to 3-pentenenitrile. The data show that selectivity to 3-pentenenitriles decreases as the sodium content of the aluminum oxide catalysts increases.

Examples 16 to 19 were performed in order to assess the impact of alkali and alkaline earth modifications to aluminium oxide catalysts used to catalyze the isomerization of cis-2-pentenenitrile.

Example 16

The experiment was conducted in a 10 mL serum bottle, using a temperature-regulated aluminum heating block. Mixing was accomplished using a magnetic stir bar. The heating block was enclosed in a nitrogen purge box. The serum bottle was charged with WN-6 (commercially available from SigmaAldrich) aluminum oxide 0.5 g, and cis-2-pentenenitrile (4.5 grams) inside a glove-box and then transferred to the heating block at the beginning of the experiment. The temperature of the heating block was maintained at 50° C. Samples were then removed after 2 hours for analysis by gas chromatography.

Example 17

Example 16 was replicated except that sodium-modified aluminum oxide was used as the catalyst.
Preparation of Sodium Modified Alumina:

A ceramic mortar and pestle was used to prepare a sodium-modified aluminum oxide catalyst material that contained 1 percent by weight (wt %) sodium based on the combined weight percent of the precursor aluminum oxide and sodium hydroxide. The material was then dried under vacuum at minus 25 inches of mercury at 300° C. for 18 hours, and then allowed to cool under nitrogen prior to evaluation.

Example 18

Example 17 was replicated except that the alumina was modified with 1 wt % KOH.

Example 19

Example 17 was replicated except that the alumina was modified with 1 wt % Ca(OH)$_2$.

The results are presented in Table 3 below.

TABLE 3

| Example | Alkali/Alkaline (wt %) | Alkali/Alkaline | C2PN conversion (%) | 3PNs selectivity (%) | PN balance[1] |
|---|---|---|---|---|---|
| 16 | 0 | None | 14.3 | 76.8 | 100 |
| 17 | 1 | Na | 33 | 16.5 | 76 |
| 18 | 1 | K | 20.3 | 63.8 | 97 |
| 19 | 1 | Ca | 14 | 73.7 | 99 |

[1]Sum of pentenenitriles in the product divided by the sum of the pentenenitriles in the feed times 100.

The data presented in Table 3 show the effect of varying the alkali content of aluminum oxide catalysts used for isomerization of cis-2-pentenenitrile to 3-pentenenitrile. The data show that the pentenenitrile (PN) balance, a measure of the amount of pentenenitriles in the feed versus the amount of pentenenitriles in the product, is adversely affected. Likewise, it can be seen from the data in Table 3 that the selectivity of the reaction to 3-pentenenitriles is decreased by adding alkali, or alkaline earth metals to the aluminium oxide catalyst used.

Example 20

Example 5 was repeated except that Catalox SCFa-140 aluminum oxide (commercially available from Sasol), which was contaminated with 1741 ppm iron was used as the catalyst. The amount of C10-dinitriles formed was approximately 2 orders of magnitude greater than when no iron was present in the aluminum oxide sample.

Comparison of the data from Example 20 to that of Example 5 show that when iron is present on the aluminum oxide catalyst the formation of by-products formed by dimerization of 2-PN (i.e. C10-dinitriles) increases.

The invention claimed is:

1. A method for minimising the amount of pentenenitrile oligomers formed in a process for isomerizing cis-2-pentenenitrile to 3-pentenenitrile in the presence of an aluminium oxide catalyst; said method comprising isomerizing the cis-2-pentenenitrile in the presence of an aluminium oxide catalyst comprising an alkali metal and/or alkaline earth metal and/or iron, wherein the alkali metal and/or alkaline earth metal and/or iron content of the aluminum oxide catalyst, measured in the form of alkali metal oxide and/or alkaline earth metal oxide and/or iron oxide, respectively, is less than 5000 ppm by weight of the aluminum oxide catalyst, wherein the aluminum oxide catalyst comprises sodium, and wherein the sodium content is at least 5.5 ppm and less than 10 ppm by weight of the aluminum oxide catalyst.

2. The method according to claim 1 wherein the amount of pentenenitrile oligomers formed in the process for isomerizing cis-2-pentenenitrile to 3-pentenenitrile is less than 300 ppm by weight for every 10 wt % of cis-2-pentenenitrile starting material which is converted to 3-pentenenitrile and trans-2-pentenenitrile products.

3. The method according to claim 1, wherein the pentenenitrile oligomers are C10-dinitriles.

4. The method according to claim 1, wherein the aluminium oxide catalyst has an alkali metal content, measured in the form of alkali metal oxide, of less than 5000 ppm by weight of the aluminum oxide catalyst.

5. The method according to claim 3, wherein the aluminium oxide catalyst has an alkaline earth metal content, measured in the form of alkaline earth metal oxide, of less than 5000 ppm by weight of the aluminum oxide catalyst.

6. The method according to claim 3, wherein the aluminium oxide catalyst has an iron content, measured in the form of iron oxide of less than 5000 ppm of the aluminum oxide catalyst.

7. The method according to claim 1, wherein the aluminium oxide catalyst has an alkali metal and alkaline earth metal content, measured in the form of alkali metal oxide and alkaline earth metal oxide of less than 5000 ppm by weight of the aluminum oxide catalyst.

8. The method according to claim 1, wherein the alkali and alkaline earth metal content of the aluminium oxide catalyst is less than 1000 ppm by weight of the aluminum oxide catalyst.

9. The method according to claim 1, wherein the alkali metal is selected from sodium or potassium and the alkaline earth metal is selected from calcium or magnesium.

10. The method according to claim 1, wherein the aluminium oxide catalyst has an alkali metal and alkaline earth metal and iron content, measured in the form of alkali metal oxide, alkaline metal oxide and iron oxide, of less than 5000 ppm by weight of the aluminum oxide catalyst.

11. The method according to claim 1, wherein the isomerization is carried out in the liquid phase.

12. The method according to claim 1, wherein the isomerization is carried out at a temperature in the range from 50° C. to 250° C.

13. The method according to claim 1, wherein the isomerization is carried out at a temperature in the range from 120° C. to 200° C.

14. The method according to claim 1, wherein the ratio of C10-dinitriles formed (wt %)/total of 3-pentenenitriles and trans-2-pentenenitriles (PNs) formed (wt %) is about 350 or less.

15. The method according to claim 1, wherein the sodium content, measured in the form of sodium oxide (Na2O), is less than 8 ppm by weight of the aluminum oxide catalyst.

* * * * *